US005719311A

United States Patent [19]
Wu et al.

[11] Patent Number: 5,719,311
[45] Date of Patent: Feb. 17, 1998

[54] CATALYTIC PROCESSES FOR ESTERIFICATION OF CARBOXYLIC ACIDS

[75] Inventors: Kuo-Ching Wu; Wen-Chyi Lin; Chiung-Hui Huang, all of Hsinchu; Po-Yu Chen, Taoyuan Hsien, all of Taiwan

[73] Assignee: Industrial Technology Research Institute, Hsinchu, Taiwan

[21] Appl. No.: 752,013

[22] Filed: Nov. 19, 1996

[51] Int. Cl.$^6$ .................................................. C07C 67/08
[52] U.S. Cl. .............................. 560/98; 560/99; 560/127; 560/205; 560/265
[58] Field of Search .............................. 560/98, 99, 127, 560/205, 265

[56] References Cited

U.S. PATENT DOCUMENTS 5,536,856  7/1996  Harrison et al. ...................... 554/164

Primary Examiner—Samuel Barts
Attorney, Agent, or Firm—W. Wayne Liauh

[57] ABSTRACT

An improved process for the esterification of carboxylic acid and alcohols into carboxylic ester is disclosed. It comprises the steps of: (a) charging the esterification reactants into a fixed bed reactor under a predetermined reaction condition; and (b) reacting the esterification reactants in the fixed bed reactor. The fixed bed reactor contains acidic catalysts that are present in a solid phase, and the reaction condition is controlled such that (i) the reactants and the products co-exist in a gas-liquid two-phase equilibrium in the fixed bed reactor and that (ii) at least one component of the reactants is present in one phase and at least one component of the products is present in another phase. Because a phase change is always taking place concurrently with the esterification reaction; the reaction stream is maintained at a relatively uniform temperature. This greatly reduces the chances of catalyst poisoning and minimizes the formation of undesired by-products such as polymers/oligmers and ethers, which are often produced at high temperatures. The concurrent phase change also contributes to the extremely high reaction yield and selectivity, typically better than 90%, observed in the present invention.

17 Claims, No Drawings

CATALYTIC PROCESSES FOR ESTERIFICATION OF CARBOXYLIC ACIDS

FIELD OF THE INVENTION

The present invention relates to an improved method for making esters of carboxylic acids. More specifically, the present invention relates to a fixed-bed catalytic process utilizing solid acidic catalysts for the esterification of carboxylic acids with alcohols. The process disclosed in the present invention provides several distinct advantages, such as substantially improved yield, reduced waste disposal problems, and reduced production cost.

BACKGROUND OF THE INVENTION

Esters of carboxylic acids, or carboxylate, and derivatives thereof have been used in a wide variety of industrial applications, such as for use in making coatings, adhesives, perfumes, plasticizers, etc. Unsaturated carboxylic esters can also be used as monomers or intermediate raw materials in preparing resins covering a wide range of applications.

Conventionally, the processes of making carboxylic esters from carboxylic acids and alcohols can be classified into the following three main categories:

(a) Liquid-phase esterification reaction utilizing a liquid catalyst: This type of processes utilize liquid phase acid, such as sulfuric acid, phosphoric acid, sulfonic acid, or p-toluenesulfonic acid, as catalysts.

(b) Liquid phase esterification reaction utilizing a solid catalyst: This type of processes typically utilize a cationic ionic exchange resin as catalyst. Examples of this type of processes include those disclosed in Japan Laid-Open Patent Application 2-279654 and European Patent EPO-10,953.

(c) Gas phase esterification reaction: This type of processes utilize a variety of catalysts such as heteropolyacids (Japan Laid-Open Patent Application 57-99556), oxides (Japan Laid-Open Patent Application 51-76019), liquid phase acids carried by a solid carrier (UK Pat. No. 1,017,806; U.S. Pat. No. 5,151,547; Japan Laid-Open Patent Application 43-20286), and zeolite (SU 1719393) in a gas phase reaction.

One of the problems associated with the liquid-catalyst liquid-phase esterification reaction is that the acidic liquid catalysts of sulfuric acid or p-toluenesulfonic acid can cause corrosion problems to the reactor. These liquid acid catalysts are also discharged along with the reaction products, thus causing severe waste disposal and pollution problems. Furthermore, because the esterification of carboxylic acids involves a reversible reaction, in order to increase the conversion rate of carboxylic acids, either excessive amounts of alcohols must be used, or the product from the esterification reaction must be constantly removed from the reaction system. In either case, the production cost of carboxylic esters is substantially increased.

The solid-catalyst, liquid-phase esterification reaction, which typically utilizes a cationic ionic exchange resin as catalyst, ameliorates the corrosion and waste disposal problems experienced with the liquid-catalyst liquid-phase processes, and results in simplified separation procedure required between the reaction product and catalysts. However, cationic ion-exchange resins typically exhibit relatively poor heat-resistance, and they often lose substantial activity after being subject to heat. Once the catalytic activity of the cationic ion-exchange resins is reduced, it is difficult to be regenerated. Furthermore, during the solid-catalyst, liquid-phase esterification process, reaction products cannot be removed from the reaction stream so as to favorably change the reaction equilibrium, and the reaction yield can only be improved by separating unreacted reactants from the product stream and recycling the unreacted reactants. This causes the production cost to be maintained at a relatively high level.

In the gas phase esterification reaction, the reaction conditions are maintained so that all the reactants and products are in the gas phase. Typically, inorganic materials are utilized as catalysts which typically exhibit excellent heat resistance and can be easily separated from the reaction products. However, the gas phase reaction necessitates a relatively large reaction vessel, resulting in large capital investment cost. Furthermore, if the gas phase esterification reaction is utilized to produce unsaturated carboxylic esters, the high reaction temperature often causes undesired by-products of polymers or oligmers to be produced. In certain instances, the high reaction temperature has caused the alcohol molecules to be dehydrated to become ethers. These side-reactions will tend to cause the reaction catalysts to lose their activity and result in operational difficulties.

SUMMARY OF THE INVENTION

The primary object of the present invention is to develop an improved process for preparing carboxylates from carboxylic acids and alcohols. More specifically, the primary object of the present invention is to develop an improved process for the preparation of carboxylates from carboxylic acids and alcohols which eliminates or minimizes many of the problems, such as corrosion, waste disposal, generation of undesired side-products, etc., often experienced in the prior art processes. The process disclosed in the present invention also improves the service life of the catalysts used in the esterification process, reduces reaction time, and substantially increases the reaction yield. The increase in reaction yield provided by the process disclosed in the present invention reduces the effort required for post-reaction separations, and further reduces the production cost.

The process disclosed in the present invention for the esterification of carboxylic acids involves a gas-liquid-solid three-phase reaction environment. The solid phase, which preferably is provided in the form of a fixed bed reactor, comprises a solid acidic catalyst whose surface is covered, via diffusion and other mass transfer mechanisms, with molecules of reaction components, which comprise both reactants (carboxylic acids and alcohols) and products (carboxylic esters and water). In the present invention, the reaction conditions are controlled such that at least one of the reaction components is present as a liquid phase and at least one of the reaction components is present as a gas phase, and the esterification reaction is accomplished through interfacial diffusion at the catalyst surface. Thermodynamically speaking, it is a well accepted terminology that a component is "present as a gas phase" when the vapor pressure of that component at the reaction temperature is greater than the reaction pressure, so that it is present thermodynamically and predominantly in the gas phase. Similarly, a component is "present as a liquid phase" when the vapor pressure of that component at the reaction temperature is lower than the reaction pressure, so that it is present thermodynamically and predominantly in the liquid phase.

In one preferred embodiment of the present invention, the reaction conditions are controlled such that the carboxylic acid is present as a liquid phase, and the alcohol, carboxylic ester, and water are present as a gas phase. In another preferred embodiment of the process disclosed in the present invention, the reaction conditions are controlled such that carboxylic acid, alcohol, and carboxylic ester are present as liquid phase, and water is present as a gas phase. It is further preferred that all the reactants (or products) are in the same phase, while at least one of the products (or reactants) is in another phase. In all cases, of course, the acidic catalysts are present as a solid phase. One of the key elements of the present invention is that, since the reaction condition is controlled such that at least one of the reactants and at least one of the products will be in different phases, a phase change will always accompany the reaction. This concurrent phase change helps the reaction stream to maintain at a relatively uniform temperature, thus greatly reducing the degree of catalyst poisoning as well as minimizing the production of undesired by-products such as polymers/oligmers and ethers. The concurrent phase change also contributes to the extremely high reaction yield, typically better than 90%, observed in the present invention.

In the present invention, the acidic catalyst can be zeolite or zeolite/resin mixture. However, the key element of the present invention is to control the reaction condition utilizing a fixed bed of acidic catalysts so as to effectuate a phase change concurrent with the esterification reaction. The selection of catalyst is not critical. Other catalysts can also be used if they exhibit satisfactory temperature stability.

DETAILED DESCRIPTION OF THE PREFERRED EMBODIMENT

The present invention discloses an improved process for the preparation of carboxylic esters from carboxylic acids and alcohols which eliminates or minimizes many of the problems experienced in the prior art processes. The problems solved by the process disclosed in the present invention include corrosion problems, liquid waste disposal problems, productions of undesired side-products such as polymers/oligmers and ethers, etc. Other advantages of the process disclosed in the present invention include improvement the service life of the catalysts used in the esterification process, reduction of reaction time required, the excellent reaction yield, and reduced effort required for recycling and separation.

In the present invention, which involves a three-phase reaction for the esterification of carboxylic acids, comprises a solid phase, and a liquid phase which is in equilibrium with a gas phase. The solid phase, which preferably is provided in the form of a fixed bed reactor, comprises a solid acidic catalyst whose surface is covered, via diffusion and other mass transfer mechanisms, with molecules in a reaction stream, which comprise both reactants (carboxylic acids and alcohols) and products (carboxylic esters and water). The acidic catalyst can be zeolite or a zeolite/resin mixture. However, the selection of the acidic catalysts is not critical. Other catalysts can also be utilized if they exhibit satisfactory temperature stability.

One of the key elements of the present invention is to control the reaction conditions so that at least one of the components in the reaction stream is present as a liquid phase and at least one of the components in the reaction stream is present as a gas phase, and the esterification reaction is accomplished through interfacial diffusion and other mass transfer mechanisms at the catalyst surface. A component is defined as being "present as a gas phase" when the vapor pressure of that component at the reaction temperature is greater than the reaction pressure, so that it is present, thermodynamically speaking, in the gas phase. Similarly, a component is defined as being "present as a liquid phase" when the vapor pressure of that component at the reaction temperature is less than the reaction pressure, so that it is present thermodynamically predominantly in the liquid phase. In one preferred embodiment of the present invention, the reaction conditions are controlled such that the carboxylic acid is present as a liquid phase, and the alcohol, carboxylic ester, and water are present as a gas phase. In another preferred embodiment of the process disclosed in the present invention, the reaction conditions are controlled such that carboxylic acid, alcohol, and carboxylic ester are present as liquid phase, and water is present as a gas phase. It is further preferred that all the products are in the same phase, while at least one of the reactants is in another phase. In all cases, the acidic catalysts are present as a solid phase.

In the present invention, since the reaction condition is controlled such that at least one of the reactants and at least one of the products are in different phases, a phase change is taking place concurrently with the esterification reaction. This concurrent phase change allows the reaction stream to be maintained at a relatively uniform temperature. This greatly reduces the chances of catalyst poisoning and minimizes the formation of undesired by-products such as polymers/oligmers and ethers, which are often produced at high temperatures. The concurrent phase change also contributes to the extremely high reaction yield and selectivity, typically better than 90%, observed in the present invention.

In the present invention, the conversion, yield, and selectivity are defined as follows. These definitions are consistent with those that have been conventionally accepted.

conversion (mol %) =

$$\frac{\text{moles of carboxylic acid in the feed} - \text{moles of carboxylic acid in the product}}{\text{moles of carboxylic acid in the feed}} \times 100\%$$

selectivity (mol %) =

$$\frac{\text{moles of carboxylate in the product}}{\text{moles of carboxylic acid in the feed} - \text{moles of carboxylic acid in the product}} \times 100\%$$

$$\text{yield (mol \%)} = \frac{\text{moles of carboxylate in the product}}{\text{moles of carboxylic acid in the feed}} \times 100\%$$

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1

200 g of $ZrOCl_2 \cdot 8H_2O$ was dissolved in 2.5 liters of water, into which ammonia water was gradually added in the presence of a pH meter. The addition of ammonia water was stopped when the pH meter read 10, and the mixture was stirred for 30 minutes then lied still for 24 hours. The precipitates were rinsed with deionized water to remove all the chloride ions (as measured using 0.1 N $AgNO_3$ titration until no precipitate was observed), filtered and dried at 100° C. for 24 hours.

50 g of the precipitates obtained above were mixed with 750 ml of 1 N sulfuric acid, stirred for 3 hours and filtered.

The filter cake was dried at 110° C. for 24 hours, and calcined at 650° C. in the presence of air for 3 hours. The final product was a $SO_4^=/ZrO_2$ catalyst. The $SO_4^=/ZrO_2$ catalyst obtained above was crushed and 7 ml of the crushed $SO_4^=/ZrO_2$ catalysts at 30–40 mesh were placed inside a ⅜" stainless steel tube to form a fixed bed reactor.

A reactant composition containing methanol and methacrylic acid at methanol/methacrylic acid mole ratio of 3 was prepared and charged into the fixed bed reactor from the upper portion thereof at a feed velocity LHSV (liquid hourly space velocity) =1 $hr^{-1}$. The temperature of the fixed bed reactor was controlled at 130° C., and the pressure of the fixed bed reactor was maintained such that the methacrylic acid was in the liquid phase, and methanol, methyl methacrylate, and water (the latter two are reaction products) were in the gas phase. After the reaction was completed in the fixed bed reactor, the reaction product flowed out of the fixed bed reactor, cooled and collected in a collecting vessel. The liquid product was analyzed using a gas chromatography, and the results are summarized in Table 1:

TABLE 1

| | |
|---|---|
| Reaction temperature (°C.) | 130 |
| Methanol/methacrylic acid mole ratio | 3 |
| LHSV ($hr^{-1}$) | 1 |
| Conversion of methacrylic acid (mol %) | 99.14 |
| Selectivity of methacrylate ester (mol %) | 99.47 |

Table 1 shows that excellent conversion (99.14 mol %) and selectivity (99.47%) were obtained using the novel process disclosed in the present invention.

COMPARATIVE EXAMPLE 1

5 g of the crushed $SO_4^=/ZrO_2$ catalysts at 30–40 mesh obtained in Example 1 were placed inside a high-pressure reaction vessel. A reactant composition containing 100 g of methanol and methacrylic acid at methanol/methacrylic acid mole ratio of 3 was charged into the high-pressure reactor. The high-pressure reactor was closed and the reaction temperature inside the reactor was controlled at 130° C. After reacting at 250 rpm for 6 hours, the reaction product was cooled and discharged from the reactor. The liquid product was analyzed using a gas chromatography and the results are summarized in Table 2:

TABLE 2

| | |
|---|---|
| Reaction temperature (°C.) | 130 |
| Methanol/methacrylic acid mole ratio | 3 |
| Catalyst concentration (wt %) | 5 |
| Reaction Time (hr) | 6 |
| Conversion of methacrylic acid (mol %) | 76.13 |
| Selectivity of methacrylate ester (mol %) | 99.42 |

EXAMPLE 2

In an aqueous solution containing 20 g of $Al_2(SO_4)_3$ .$18H_2O$, 180 g of another aqueous solution contain sodium silicate (water glass) and 3 g of tetrapropyl ammonium bromide were added. The second aqueous solution was prepared such that the mole ratio between silicon oxide and aluminum oxide in the final mixture would be 30. The pH of the mixture was properly adjusted by adding drops of sulfuric acid. After reacting at 160°–180° C. in a 2-liter high-pressure vessel for 24 hours, the reaction product was removed from the reactor, filtered, rinsed, and baked at 500° C. for 12 hours. The reaction product was a NaZSM-5 solid, which was subject to an ion-exchange process at 80° C. in ammonium nitrate solution to form $NH_4ZSM$-5. After calcining at 550° C. for 12 hours, the $NH_4ZSM$-5 solid became HZSM-5 zeolite. The HZSM-5 zeolite obtained above was crushed and 7 ml of the crushed HZSM-5 zeolite at 30–40 mesh were placed inside a ⅜" stainless steel tube to form a fixed bed reactor.

A reactant composition containing ethanol and propionic acid at an ethanol/propionic acid mole ratio of 1.5 was charged into the fixed bed reactor from the upper portion thereof at a feed velocity LHSV (liquid hourly space velocity) =1 $hr^{-1}$. The temperature of the fixed bed reactor was controlled at 110° C., and the pressure of the fixed bed reactor was maintained such that the propionic acid was in the liquid phase, and ethanol, ethyl propionate, and water were in the gas phase. After the reaction was completed in the fixed bed reactor, the reaction product flowed out of the fixed bed reactor, cooled, and collected in a collecting vessel. The liquid product was analyzed using a gas chromatography, and the results are summarized in Table 3:

TABLE 3

| | |
|---|---|
| Reaction temperature (°C.) | 110 |
| Methanol/methacrylic acid mole ratio | 1.5 |
| LHSV ($hr^{-1}$) | 1 |
| Conversion of propionic acid (mol %) | 96.38 |
| Selectivity of ethyl propionate ester (mol %) | 99.72 |

Table 3 shows that excellent conversion (96.38 mol %) and selectivity (99.72%) were also obtained for the ethyl alcohol/propionic acid system using the process disclosed in the present invention.

COMPARATIVE EXAMPLE 2

5 g of the crushed HZSM-5 zeolite at 30–40 mesh obtained in Example 2 were placed inside a 150-ml high-pressure reaction vessel. A reactant composition containing 100 g of ethanol and propionic acid at ethanol/propionic acid mole ratio of 1.5 was charged into the high-pressure reactor. The high-pressure reactor was closed and the reaction temperature inside the reactor was controlled at 110° C. After reacting at 250 rpm for 4 hours, the reaction product was cooled and discharged from the reactor. The liquid product was analyzed using a gas chromatography, and the results are summarized in Table 4:

TABLE 4

| | |
|---|---|
| Reaction temperature (°C.) | 110 |
| Methanol/methacrylic acid mole ratio | 1.5 |
| Catalyst concentration (wt %) | 1 |
| Reaction Time (hr) | 4 |
| Conversion of methacrylic acid (mol %) | 66.36 |
| Selectivity of methacrylate ester (mol %) | 99.56 |

EXAMPLE 3

In Example 3, 7 ml of Nation NR-50 (from Mobil Oil Co.) were placed inside a ⅜" stainless steel tube to form a fixed bed reactor. A reactant composition containing isobutanol and hexahydrophthalic anhydride at an alcohol/carboxylic anhydride mole ratio of 3 was charged into the fixed bed reactor from the upper portion thereof at a feed velocity LHSV (liquid hourly space velocity)=1 $hr^{-1}$. The temperature of the fixed bed reactor was controlled at 110° C., and the pressure of the fixed bed was maintained such that hexahydrophthalic anhydride and isobutyl hexahydrophthalate ester were in the liquid phase, and isobutanol and water were in the gas phase. After the reaction was completed in the fixed bed reactor, the reaction product flowed out of the fixed bed reactor, cooled and collected in a collector vessel. The liquid product was analyzed using autotitration (by measuring acid values) and the results are summarized in Table 5:

TABLE 5

| Reaction temperature (°C.) | 110 |
| Mole ratio of isobutanol/hexahydrophthalic anhydride | 3 |
| LHSV (hr$^{-1}$) | 1 |
| Yield of isobutyl hexahydrophthalate (mol %) | 96.46 |

EXAMPLE 4

290 ml of Ti[OCH(CH$_3$)$_2$]$_4$ were dissolved in 2 liters of water. After the addition of 250 ml of concentrated sulfuric acid solution, drops of ammonia water were gradually added in the presence of a pH meter. The addition of ammonia water was stopped when the pH meter read 8, and the mixture was stirred for 30 minutes and lied still for 24 hours. The precipitates were rinsed with deionized water, filtered and dried at 100° C. for 24 hours.

20 g of the precipitates obtained above were mixed with 300 ml of 1 N sulfuric acid, stirred for 3 hours and filtered. The filter cake was dried at 110° C. for 24 hours, and finally baked at 625° C. in the presence of air for 3 hours. The final product was a SO$_4^=$/TiO$_2$ catalyst. The SO$_4^=$/TiO$_2$ catalyst. The SO$_4^=$/TiO$_2$ catalyst obtained above was crushed and 7 ml of the crushed SO$_4^=$/TiO$_2$ catalysts at 30–40 mesh were placed inside a ⅛" stainless steel tube to form a fixed bed reactor.

A reactant composition containing isooctyl alcohol and phthalic anhydride at an isooctyl alcohol/phthalic anhydride mole ratio of 3 was charged into the fixed bed reactor from the upper portion thereof at a feed velocity LHSV (liquid hourly space velocity)=1 hr$^{-1}$. The temperature of the fixed bed reactor was controlled at 160° C., and the pressure of the fixed bed was maintained such that the isooctyl alcohol, phthalic anhydride and isooctyl phthalate were in the liquid phase, and water was in the gas phase. After the reaction was completed in the fixed bed reactor, the reaction product flowed out of the fixed bed reactor, cooled and collected in a collector vessel. The liquid product was analyzed using autotitration (by measuring acid values), and the results are summarized in Table 6:

TABLE 6

| Reaction temperature (°C.) | 130 |
| Mole ratio of isooctyl alcohol and phthalic anhydride | 3 |
| LHSV (hr$^{-1}$) | 1 |
| Conversion of phthalic anhydride (mol %) | 92.82 |

Both Tables 5 and 6 show that conversions of better than 90 mol % were obtained.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A process for preparing esterification products, which comprise at least one carboxylic ester, from esterification reactants, which comprise at least one alcohol and at least one carboxylic acid or carboxylic anhydride, comprising the steps of:

(a) charging said esterification reactants into a fixed bed reactor under a predetermined reaction condition;

(b) reacting said esterification reactants in said fixed bed reactor to form esterification products, which comprise an ester and water;

(c) wherein said fixed bed reactor comprises acidic catalysts that are present in a solid phase;

(d) further wherein said reaction condition is controlled such that (i) said reactants and said products co-exist in a gas-liquid two-phase equilibrium in said fixed bed reactor, (ii) at least one component of said reactants is present in a liquid phase, and (iii) both said esterification products of ester and water are present in a gas phase.

2. The process for preparing esterification products according to claim 1 wherein said alcohols are selected from the group consisting of straight-chain, branched and aromatic alcohols having a carbon number from C1–C20.

3. The process for preparing esterification products according to claim 1 wherein said carboxylic acids are selected from the group consisting of straight-chain, branched and aromatic carboxylic acids having a carbon number from C3–C20.

4. The process for preparing esterification products according to claim 1 wherein said acidic catalyst comprises at least one member selected from the group consisting of oxides, zeolites, and resins.

5. The process for preparing esterification products according to claim 1 wherein said alcohols contain less than five hydroxy groups.

6. The process for preparing esterification products according to claim 1 wherein said carboxylic acids contain less than three carboxylic groups.

7. The process for preparing esterification products according to claim 1 wherein said alcohols contain less than two hydroxy groups.

8. The process for preparing esterification products according to claim 1 wherein said alcohols have a carbon number from C1–C12.

9. The process for preparing esterification products according to claim 1 wherein said carboxylic acids contain less than two carboxylic groups.

10. The process for preparing esterification products according to claim 1 wherein said carboxylic acids have a carbon number from C3–C20.

11. The process for preparing esterification products according to claim 1 wherein said reactants comprise methanol and methacrylic acid, said products comprise methyl methacrylate and water, and said reaction condition is controlled such that said methacrylic acid is in said liquid phase, and said methanol, methyl methacrylate, and water are in said gas phase.

12. The process for preparing esterification products according to claim 11 wherein catalyst comprises a SO$_4^=$/ZrO$_2$ oxide.

13. The process for preparing esterification products according to claim 1 wherein said reactants comprise ethanol and propionic acid, said products comprise ethyl propionate and water, and said reaction condition is controlled such that said propionic acid is in said liquid phase, and said ethanol, ethyl propionate, and water are in said gas phase.

14. The process for preparing esterification products according to claim 13 wherein catalyst comprises a HZSM-5 zeolite.

15. The process for preparing esterification products according to claim 1 wherein said reactants comprise isobutanol and hexahydrophthalic anhydride, said products comprise isobutyl hexahydrophthalate and water, and said reaction condition is controlled such that said hexahydrophthalic anhydride and isobutyl hexahydrophthalate are in said liquid phase, and isobutanol and water are in said gas phase.

16. The process for preparing esterification products according to claim 1 wherein said reactants comprise isooctyl alcohol and phthalic anhydride, said products comprise isooctyl phthalate and water, and said reaction condition is controlled such that said isooctyl alcohol, phthalic anhydride and isooctyl phthalate are in said liquid phase, and water is in said gas phase.

17. The process for preparing esterification products according to claim 16 wherein catalyst comprises a $SO_4^=/TiO_2$ oxide.

* * * * *